United States Patent

Pomerantz

[11] Patent Number: 5,882,627
[45] Date of Patent: Mar. 16, 1999

[54] METHODS AND COMPOSITIONS FOR IN-VIVO DETECTION OF ORAL CANCERS PRECANCEROUS CONDITIONS

[75] Inventor: Edwin Pomerantz, Woodland Hills, Calif.

[73] Assignee: Zila Pharmaceuticals, Inc., Phoenix, Ariz.

[21] Appl. No.: 930,437

[22] PCT Filed: Jan. 16, 1996

[86] PCT No.: PCT/US96/00509

§ 371 Date: Sep. 3, 1997

§ 102(e) Date: Sep. 3, 1997

[87] PCT Pub. No.: WO97/26018

PCT Pub. Date: Jul. 24, 1997

[51] Int. Cl.⁶ .................................................. A61K 49/00
[52] U.S. Cl. ........................ 424/9.7; 424/9.6; 424/9.1; 424/10.3
[58] Field of Search .............................. 424/9.6, 9.1, 9.7, 424/10.3; 544/56, 59

[56] References Cited

U.S. PATENT DOCUMENTS 3,852,413 12/1974 Cammarata ............................. 424/1.69
4,321,251 3/1982 Mashberg ................................. 424/9.7
5,372,801 12/1994 Malmros et al. ....................... 424/9.7

Primary Examiner—Jose' G. Dees
Assistant Examiner—Michael G. Hartley
Attorney, Agent, or Firm—Drummond & Duckworth

[57] ABSTRACT

A method for in-vivo detection of premalignant oral lesions and oral carcinomas includes the step of applying to oral tissue a non-toxic dye other than toluidine blue O, selected from compounds having structure

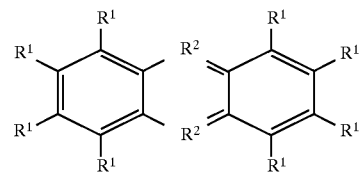

and ionic derivatives thereof, wherein $R^1$ is H, or lower alkyl group or $N(R^3)_2$, $R^2$ is N, S or O, and $R^3$ is H or a lower alkyl group.

7 Claims, No Drawings

METHODS AND COMPOSITIONS FOR IN-VIVO DETECTION OF ORAL CANCERS PRECANCEROUS CONDITIONS

This invention relates to in vivo methods for detection of premalignant oral lesions and oral carcinomas.

In another respect the invention pertains to compositions for carrying out such diagnostic procedures.

In another aspect the invention relates to such in vivo diagnostic procedures and compositions useful therein which are especially useful in screening patients for possible oral cancer as part of routine dentist's or physician's examinations, or procedures such as periodic check-up's, dental cleaning, etc.

In yet another aspect the invention relates to such procedures and compositions which utilize dye stains which are more readily available and/or less expensive and less complicated to synthesize and/or purify then the dyes employed in prior art procedures.

In yet another respect the invention concerns such in vivo procedures and compositions employing dyes which are less potentially toxic than prior art fluorescein derivatives and methylene blue and which may, therefore, be applied by rinsing the entire oral cavity and/or gargling.

In-vivo diagnostic procedures for detection of premalignant oral lesions or oral carcinomas, employing dye compositions which are selectively retained by tissues rendered abnormal due to dysplasia, hyperplasia, tumorigenesis, and other active surface lesions, are known in the art. For example, procedures employing fluorescein or fluorescein derivatives are disclosed in Chenz, Chinese Journal of Stomatology (27:44–47 (1992)) and Filiurin (Stomatologiia (Russian) 72:44–47 (1993)). These procedures involve application of the dye, followed by examination under ultraviolet light to detect the cancerous/precancerous tissue, which is selectively fluorescent.

Another prior art procedure involves in-vivo application by rinsing with toluidine blue O, followed by normal visual examination to detect any selectively stained tissue. Such procedures are disclosed, for example in the U.S. Patent to Tucci, et al. U.S. Pat. No. 5,372,801 and in U.S. Pat. No. 4,321,251 to Mashberg. Toluidine blue, has been used for decades as a histopathological stain for in-vitro use. Through this use it has become known as a metachromatic dye, staining nuclei rich in DNA and RNA a purple to pink color. The inherent deep blue color of toluidine blue is changed to purple or pink when the dye is bound to a nucleic acid or other acidic cellular macromolecule. Of course, this type of staining is dependent on the dye gaining access to internal subcellular structures such as the nucleus. Such access is readily obtained only by "fixing" a tissue sample of formaldehyde or other reagent that disrupts the cellular membrane without destroying general cellular structure.

In contrast to the mechanism involved with in-vitro use, the staining of oral tissue in-vivo by toluidine blue O is due to its ability to penetrate the enlarged and more accessible interstitial spaces of dysplastic tissue, which retains the dye longer than areas containing normal tissue with its tight intercellular junctions. Empirically, the observation is made that toluidine blue simply does not penetrate normal intercellular spaces efficiently than those of normal tissue, and becomes temporarily localized, it diffuses out with time and does not remain bound to the cells as it would if it actually "stained" acidic substructures.

The Mashberg procedure involves application of the toluidine blue O solution as a rinse of the entire oral cavity, with gargling, following by rinses with water and acidic acid to remove the dye which is not retained by the cancerous or precancerous tissue. The preliminary Mashberg diagnosis is then confirmed by direct application of the toluidine blue O composition to the suspect site 10–14 days later.

The Tucci '801 patent discloses an improved toluidine blue O composition for use according to the general Mashberg procedure.

An in-vivo procedure involving use of Lugol's solution (iodine) and toluidine blue O was proposed for detecting esophageal cancer synchronous with upper aerodigestive tract cancers in Papazian (Gastroenterologie Clinique et Biologique (9:16–22, 1985). Because of possible toxic properties of fluorescein, iodine and methylene blue, it is considered that they are not suitable for indiscriminate application by oral rinse and/or gargling procedures. Toluidine blue O is not toxic, but has been expensive to synthesize and purify in commercial quantities.

Accordingly, it would be advantageous to employ dyes other than fluorescein, fluorescein derivatives, iodine, methylene blue or toluidine blue O in diagnostic procedures for in-vivo detection of premalignant oral lesions and oral carcinomas.

I have now discovered that non-toxic dyes other than methylene blue or toluidine blue O, selected from compounds having the structure

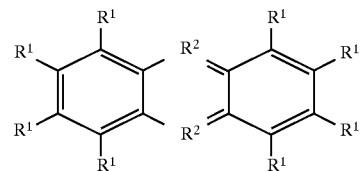

and ionic derivatives thereof, wherein $R^1$ is H, a lower alkyl group or $N(R^3)_2$, $R^2$ is N, S or O, and $R^3$ is H or a lower alkyl group, are effective for in-vivo detection of premalignant oral lesions or oral carcinomas. The lower alkyl groups can be $C_1$–$C_4$, straight or branched chain groups, preferably methyl or ethyl groups. In general, these dyes are employed according to the same general procedure as disclosed by the Mashberg '251 patent, i.e., by sequentially rinsing the oral cavity with the dye stain composition, which is selectively retained by cancerous and precancerous tissues, and then rinsing the oral cavity to remove unretained stain composition.

The determination of whether a particular dye having the above-described structure is selectively retained can be readily ascertained by persons skilled in the art without undue experimentation, by using the dye in accordance with the general Mashberg procedure, described above. The potential toxicity of a particular dye can be readily determined by art-recognized techniques and standards, e.g., animal feeding studies.

Suitable compositions for the application of the dyes defined above are prepared by mixing the dye with a pharmaceutically acceptable oxidizing agent which oxidizes any leuco form of the dye to the chromo form. The oxidizing agents are selected to be pharmaceutically acceptable, i.e., are non-toxic and do not cause undesirable side reactions which degrade the dye. Those skilled in the art will be able to identify suitable oxidizing agents for use in accordance with the invention by routine tests of known non-toxic mild oxidants. For example, in accordance with the presently preferred embodiment of the invention it is preferred to use hydrogen peroxide, either directly or by reaction of known peroxide precursors with water in the compositions, e.g., water soluble "per" compounds, such as urea peroxide, sodium perborate tetrahydrate, sodium percarbonate, calcium peroxide and the like.

The compositions of the invention are preferably formulated to yield a final solution which is substantially isotonic and has a pH in the range of approximately 2.5 to 7.0, preferably 4.0 to 5.0. This is accomplished by adding an appropriate water soluble buffer system. The presently preferred buffer system is acetic acid-sodium acetate. Other suitable buffer systems include citric acid-sodium citrate, or mixed acid-salt systems such as citric acid-sodium phosphate and the like.

The solvent used to provide liquid dye compositions is an aqueous solvent. According to the preferred embodiment of the invention, the solvent includes a pharmaceutically acceptable, i.e., non-toxic, non-reactive, alcohol, e.g., ethyl alcohol. Such solvents do not appreciably interfere with the tissue staining mechanism and do not themselves contribute to the reduction of chromo forms of the dyes to the leuco forms.

Flavoring, stable to the oxidizing agent, may be added to improve the palatability of the dye solution if it is to be used as a "rinse".

The amount of the dye in the liquid compositions is preferably adjusted to yield a concentration of approximately 1% by weight in the final composition, although higher concentrations can be employed and lower concentrations are at least partially effective, e.g., from about 0.5 to about 3.5 weight %.

Surprisingly, dyes having the above-defined structure, which are closely related to toluidine blue O, e.g., methylene blue and thionine, have proven to be ineffective, whereas other dyes closely related to toluidine blue O, e.g., Brilliant Cresyl Blue, Azure A, Azure B and Azure C are effective.

According to my present knowledge, Azure B and Azure C are employed in accordance with the presently preferred embodiment of the invention.

The invention also contemplates compositions for use in accordance with the methods of the invention and processes for manufacturing such composition, in which any leuco form of the dye present in the composition is oxidized to the chromo form, by inclusion of a pharmaceutically acceptable oxidizing agent in the composition, in the manner analogous to that disclosed in the Tucci et al. U.S. Pat. No. 5,372,801.

EXAMPLES

The following examples are presented in order to illustrate practice of the invention to those skilled in the art and not by way of limitation on the scope thereof.

Example 1

Test compositions of Azure B, Azure C, Brilliant Cresyl Blue ("BCB") and thionine dyes and a control composition, toluidine blue O dye ("TBO") are prepared by mixing each of the dyes with the indicated ingredients in the following proportions (% by weight):

| Ingredient | % by Weight |
| --- | --- |
| Purified Water, U.S.P. | 83.86 |
| Glacial Acetic Acid, U.S.P. | 4.61 |
| Sodium Acetate Trihydrate, U.S.P. | 2.45 |
| SD18 Ethyl Alcohol | 7.48 |
| Hydrogen Peroxide 30%, U.S.P. | 0.41 |
| IFF Raspberry IC563457 | 0.20 |
| Dye | 1.00 |

Example 2

A rinse solution is prepared by mixing the following ingredients in the indicated proportions (weight %):

| Purified Water, U.S.P. | 98.70 |
| --- | --- |
| Glacial Acetic Acid, U.S.P | 1.00 |
| Sodium Benzoate, U.S.P. | 0.10 |
| IFF Raspberry IC563457 | 0.20 |

Example 3

The clinical effectiveness of each of the test mixtures, compared to the TBO control mixture, is determined, utilizing the Mashberg protocol.

Patients are first screened for oral pathology employing the TBC control mixture. After identifying potential cancerous or precancerous pathology, all traces of the TBO are removed by repeated rinses with water and the acetic acid rinse solution. Those patients exhibiting oral pathology are then used as test subjects for each of the test mixtures. 2–3 cc of each test mixture is applied by painting the pathologic mucosal surfaces, followed by rinsing with the rinse mixture and water to remove excess dye composition. After examination with each dye and before testing with the next dye, all traces of the dye are removed from the lesion by repeated rinsing with the rinse mixture and water.

The Azure B test mixture provides equivalent staining intensity to TBO, localization of the lesions and delineation of the borders of the lesions. Adjacent unstained tissue shows slight dye accumulation, but not to the detriment of lesion discrimination.

The Azure C test mixture provides equivalent staining intensity to TBO, localization of the lesions and delineation of the borders of the lesions. Adjacent, uninvolved tissues are stained to a red/purple hue, but not to the detriment of lesion discrimination.

The Brilliant Cresyl Blue test mixture provides results similar to Azure B and Azure C.

The Thionine test mixture provides a warm red background stain on both the stained and unstained tissues, such that the discrimination of the lesion borders is insufficient.

Example 4

The procedures of Example 3 are repeated, except that the test and control compositions are applied to the oral mucosa by rinsing, with gargling, instead of by direct application to the locus of the suspect sites. Equivalent results are obtained.

Having disclosed my invention in such terms as to enable those skilled in the art to make and use it, and, having identified the presently preferred embodiments thereof, I claim:

1. In a method for in vivo detection of premalignant oral lesions and oral carcinomas, including the steps of sequentially rinsing the oral cavity with a dye stain composition which is selectively retained by cancerous and precancerous oral tissues, wherein the stain composition consists essentially of toluidine blue O, and rinsing the oral cavity with a rinse composition for removing unretained stain composition, the improvement in which the stain composition consists essentially of a non-toxic dye other than toluidine blue O and methylene blue, selected from compounds having the structure

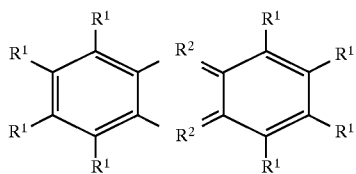

and ionic derivatives thereof, wherein $R^1$ is H, a lower alkyl group or $N(R^3)_2$, $R^2$ is N, S or O, and $R^3$ is H or a lower alkyl group.

2. A method for in vivo detection of premalignant oral lesions and oral carcinomas, including the steps of sequentially rinsing the oral cavity with a dye stain composition which is selectively retained by cancerous and precancerous oral tissues, wherein the stain composition consists essentially of toluidine blue o, and rinsing the oral cavity with a rinse composition for removing unretained stain composition, the improvement in which the stain composition consists essentially of a dye selected from the group consisting of Azure B, Azure C and Brilliant Cresyl Blue.

3. The method of claim 2 in which said dye is Brilliant Cresyl Blue.

4. The method of claim 2 in which said dye is selected from the group consisting of Azure B and Azure C.

5. The method of claim 4 in which said dye is Azure B.

6. The method of claim 4 is which said dye is Azure C.

7. A biological stain composition for in vivo detection of cancerous and precancerous tissue, comprising:

(a) a non-toxic dye other than toluidine blue O and methylene blue having the structure

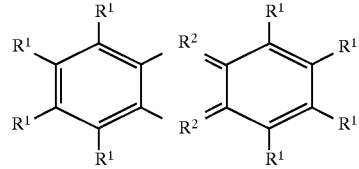

and ionic derivatives thereof, wherein $R^1$ is H, a lower alkyl group or $(R^3)_2$, $R^2$ is N, S or O, and $R^3$ is H or a lower alkyl group, and (b) a pharmaceutically acceptable oxidizing agent for leuco forms of the dye.

* * * * *